(12) United States Patent
Wilharm et al.

(10) Patent No.: US 7,289,900 B2
(45) Date of Patent: Oct. 30, 2007

(54) APPARATUS AND METHOD FOR AN AUTOMATED CETANE NUMBER DETERMINATION

(76) Inventors: Peter Wilharm, Trentiner Ring 30, 86356 Neusäss/Täfertingen (DE); Thomas Wilharm, Trentiner Ring 30, 86356 Neusäss/Täfertingen (DE)

( * ) Notice: Subject to any disclaimer, the term of this patent is extended or adjusted under 35 U.S.C. 154(b) by 0 days.

(21) Appl. No.: 11/636,234

(22) Filed: Dec. 8, 2006

(65) Prior Publication Data
US 2007/0083319 A1    Apr. 12, 2007

Related U.S. Application Data

(63) Continuation-in-part of application No. PCT/EP2006/005842, filed on Jun. 19, 2006.

(30) Foreign Application Priority Data
Jun. 20, 2005   (DE) .................. 10 2005 028 706

(51) Int. Cl.
*B60T 7/12*    (2006.01)
*F02M 7/00*    (2006.01)

(52) U.S. Cl. ...................... 701/103; 123/435

(58) Field of Classification Search ............... 701/103, 701/104; 123/198 A, 78 D, 435, 406.45, 123/406.47, 381; 73/35.02
See application file for complete search history.

(56) References Cited

U.S. PATENT DOCUMENTS

| | | | |
|---|---|---|---|
| 5,457,985 A | | 10/1995 | Cellier et al. |
| 6,609,413 B1 | * | 8/2003 | De Craecker ............... 73/35.02 |
| 7,027,906 B2 | * | 4/2006 | Araki ......................... 701/104 |
| 7,121,254 B2 | * | 10/2006 | Wickman et al. ........... 123/304 |

FOREIGN PATENT DOCUMENTS

| | | |
|---|---|---|
| DE | 197 12 921 | 10/1992 |
| DE | 197 01 288 | 7/1998 |
| WO | WO 02/14456 | 2/2002 |

* cited by examiner

Primary Examiner—John T. Kwon
(74) Attorney, Agent, or Firm—Klaus J. Bach

(57) ABSTRACT

In an apparatus and method for determining the cetane number of a fuel by combustion of a sample in a constant volume combustion chamber filled with compressed air into which the fuel is injected via a temperature controlled injection nozzle, wherein means are provided for sensing the pressure in the combustion chamber and recording it for determining the cetane number therefrom, an automated sample supplier is provided adapted to accommodate a plurality of fuel samples and including means for selectively connecting a pump to a particular sample and pressurizing it for injection into the combustion chamber and means for heating the combustion chamber and means for cooling the injector nozzle are provided for maintaining these devices at desired temperatures.

12 Claims, 1 Drawing Sheet

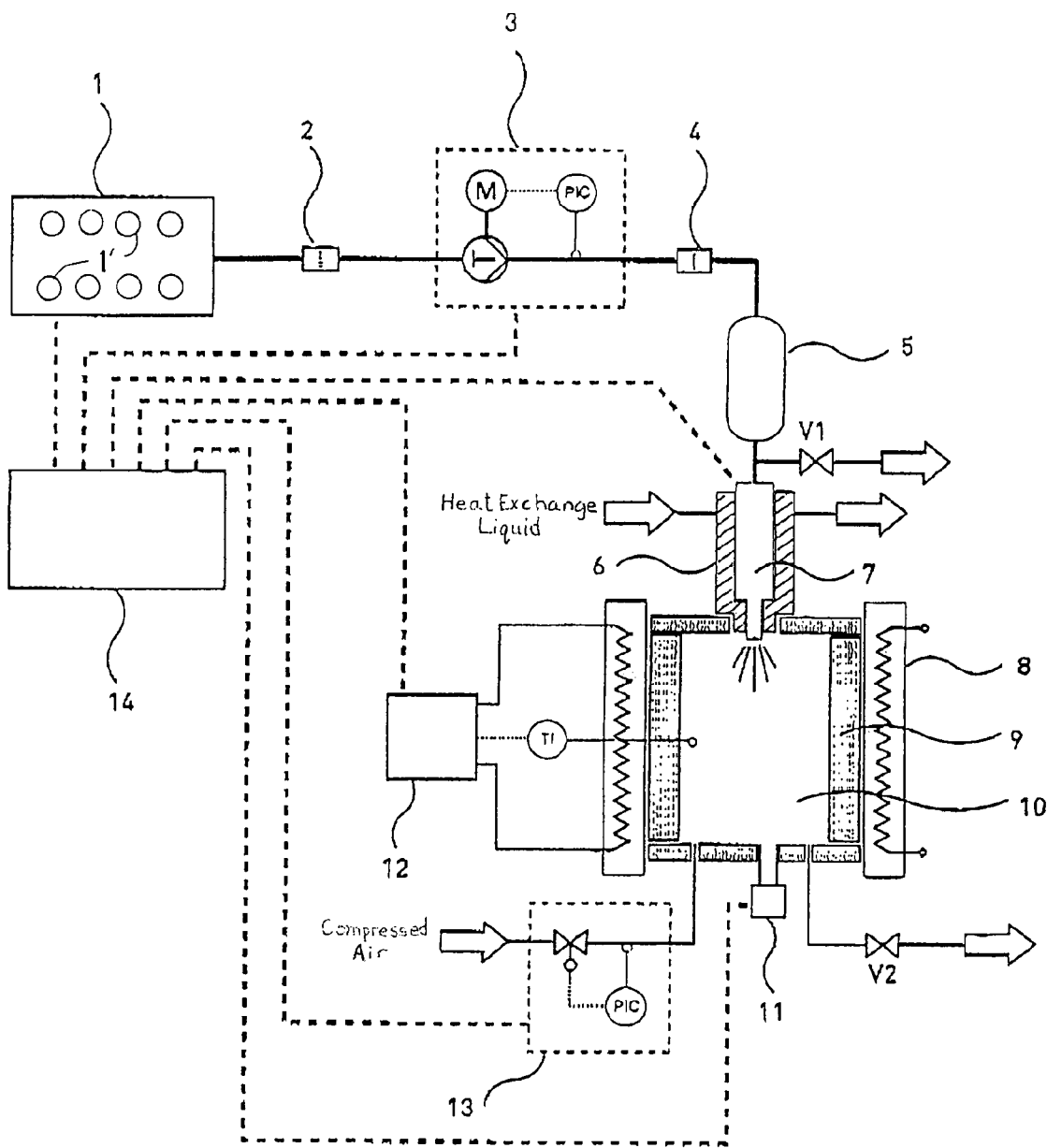

APPARATUS AND METHOD FOR AN AUTOMATED CETANE NUMBER DETERMINATION

This is a Continuation-In-Part Application of International patent application PCT/EP2006/005842 filed Jun. 19, 2006 and claiming the priority of German application 10 2005 028 706.9 filed Jun. 20, 2005.

BACKGROUND OF THE INVENTION

The present invention resides in an apparatus and method for an automated cetane number determination by means of a constant-volume combustion chamber including a fuel injection nozzle, means for filling the combustions chamber with compressed air, means for heating the combustion chamber and means for recording the pressure in the combustion chamber during ignition and combustion of sample fuel injected into the combustion chamber.

The cetane number is a measure for the ignition quality of intermediate distillates, particularly diesel fuel.

Examples for intermediate distillates are refinery products with a boiling range from about 150 to 500° C., which are commercially available as heating oil, diesel fuel, kerosene or jet fuel. Examples for bio-diesel fuels are fatty and methyl ester manufactured from rape oil, soybean oil, palm oil, suet, sun flower oil, waste food fats and mixtures thereof.

A good ignition quality of a diesel fuel means good start-up behavior, quiet operation of the diesel engine and good exhaust gas emission values.

The cetane number is defined by the norm EN ISO 5165 and its determination is described by that norm. Cetane numbers are usually determined in a standardized four cycle one-cylinder engine with variable compression ratio and indirect fuel injection. Since this engine-based method however is time-consuming and expensive attempts have been made to determine the cetane number by means of a constant volume combustion chamber method.

In a constant volume combustion chamber apparatus for determining the cetane number the measuring cycle comprises the following operating steps:

1. Filling a combustion chamber with compressed air and heating the combustion chamber,
2. injecting fuel into the combustion chamber via a fuel injection nozzle,
3. recording the combustion chamber pressure curve resulting from the fuel ignition and combustion, and
4. calculating the cetane number from the ignition delay measured.

The time delay between the fuel injection and ignition, that is, the ignition delay is measured as accurately as possible. This ignition delay is for conventional diesel fuel in a constant volume apparatus typically 3 to 10 ms. By measuring fuels with known cetane numbers under identical conditions, the apparatus can be calibrated.

The known constant volume apparatus have various disadvantages:

The use of mechanical or mechanical-electronic sensor elements which may have an actuation tolerance of up to 2 ms results in an insufficient precision in the ignition delay determination. It is tried to eliminate this disadvantage by the use of a multitude of measuring cycles with subsequent statistical evaluation.

The use of conventional injection nozzles which operate with comparatively low pressures makes the determination procedure sensitive with respect to changes in the surface tension of otherwise identical fuel samples.

With the use of conventional pump-nozzle systems, the fuel injection volume is not accurately known and can vary substantially. As a result, also statistical variations in the ignition delay occur.

The use of injection nozzles which are not temperature-controlled results in a drift of the measuring results until the injection nozzle has reached a thermal equilibrium.

For the testing of several fuel samples an automated testing procedure is not available.

In the fuel flow structures from the suction side to the injection nozzle, the known apparatus include large dead volumes. Consequently, large sample volumes are required for the cetane number determination.

It is the object of the present invention to provide an improved and more accurate and automated cetane number determination for a constant volume apparatus.

SUMMARY OF THE INVENTION

In an apparatus and method for determining the cetane number of a fuel by combustion of a sample in a constant volume combustion chamber filled with compressed air into which the fuel is injected via a temperature controlled injection nozzle, wherein means are provided for sensing the pressure in the combustion chamber and recording it for determining the cetane number therefrom, an automated sample supplier is provided adapted to accommodate a plurality of fuel samples and including means for selectively connecting a pump to a particular sample and pressurizing it for injection into the combustion chamber and means for heating the combustion chamber and means for cooling the injector nozzle are provided for maintaining these devices at desired temperatures.

The apparatus and method according to the invention provide for an automated cetane number determination with high accuracy and maximum reproducibility not achievable with the known constant volume apparatus and the methods used thereby.

The invention will be described below in greater detail with reference to the accompanying drawings.

BRIEF DESCRIPTION OF THE DRAWINGS

The sole FIGURE shows schematically the apparatus and method according to the invention.

DESCRIPTION OF A PREFERRED EMBODIMENT

The apparatus as shown in the FIGURE comprises a sample supplier 1, which automatically provides samples to be tested to the testing device via a first filter 2, a supply pump 3, a second filter 4 arranged downstream of the supply pump 3, a pressurized fuel storage 5, a high pressure valve V1, a cooling sleeve 6, an injection nozzle 7 disposed in the cooling sleeve 6, a combustion chamber 9 with a combustion chamber interior space 10, an exhaust gas valve V2, a pressure sensor 11 for sensing the pressure in the combustion chamber interior space 10, a temperature controller 12 for the combustion chamber a pressure controller 13 for the combustion chamber and a control unit 14.

Samples are automatically provided by the sample supplier 1 by withdrawing fuel from a particular sample container 1' by the supply pump 3. To this end, from a multitude of sample containers 1' present in the sample supplier 1, a particular sample container is selected by the control unit 14 and the suction line of the supply pump 3 is inserted into the particular selected container. Such automated sample suppliers are well known as so-called "auto sampler" and are commercially available in various configurations. Alternatively, an electrically controllable switch-over valve may be used. In that case, the suction line of the supply pump 3 is connected at the same time to several sample containers by way of the switch-over valve. With the switch-over valve, a certain sample can be provided under the control of the control unit 14. In an actual embodiment for example electrically controlled HPLC eluent selection valves of the company Rheodyne are used.

The first filter 2 is provided to protect the downstream supply pump 3 from malfunctioning. It has been found that diesel fuel samples may include various contaminants such as particles or metal splinters. Alternatively or additionally, the fuel sample supply line may include a fine filter (sinter metal filter).

The supply pump 3 is a single or multistage piston compressor pump as it is known from instrument analysis procedures. Such piston compressor pumps used in the HPLC analysis (HPCL high performances Liquid Chromatography) are suitable for the testing apparatus according to the invention if they can provide at an operating pressure of at least 400 bar at a flow rate>2 ml/min.

Low pulsation double piston pumps with integrated pressure control capable of providing an output pressure of at least 1600 bar are preferred. In an actual embodiment, a "Synova" pump (distributed by the company Techlab, Erkerode, Germany) is used. The supply pump 3 sucks in fuel and pressurizes the fuel to a level suitable for a piezo injection nozzle 7, which is typically to 800 to 2000 bar.

High pressure pumps as they are used in diesel engines are not desirable for the testing apparatus according to the invention because they have a relatively large dead volume. The second filter 4 is provided to retain contaminants or other particles in order to protect the injection nozzle 7 from misfunctioning. As filter elements preferably steel filter fabrics are used. Preferably a fuel filter with only a small interior volume is used so that the dead volume of the pressure line remains small.

The pressurized fuel storage container 5 is connected to the injection nozzle 7 via a pressure line of relatively small length. The storage volume is so selected that sufficient fuel for at least one injection cycle without noticeable pressure drop is provided. Another optimization criterion resides in minimizing the flushing volume of the whole apparatus. In connection with the testing of several fuel samples, after completion of the testing of one fuel sample, the whole apparatus is flushed with the fuel sample to be newly tested. If the pressure storage volume is small, less fuel and less time is required for the flushing procedure.

In the connecting line between the pressure storage 5 and the piezo nozzle 7, a high pressure valve V1 is arranged to facilitate flushing of the apparatus. It is opened under the control of the control unit 14 when the apparatus is filled with a new fuel sample.

For good repetition accuracy of the cetane number determination, it is important that the fuel in the injection nozzle 7 has a constant defined temperature up to the nozzle tip. In this way, it is ensured that a fuel sample has the same viscosity with each injection step.

The injection nozzle 7 is surrounded by a self-supporting cooling sleeve 6, which extends downwardly closely to the multi-opening nozzle structure. The cooling sleeve 6 includes bores and hollow spaces which are filled with a temperature-controlled heat carrier liquid preferably water which is conducted through the bores and spaces under pressure. With the cooling sleeve, the injection nozzle 7 can be kept at a predefined temperature in spite of a hot combustion chamber. The cooling sleeve is mechanically removably connected to the combustion chamber and the injection nozzle 7 is removably connected to the cooling sleeve 6.

The injection nozzle 7 is a commercially available piezo electric injector with a multi-opening nozzle as used for diesel engines. The piezo-injector atomizes the fuel under high pressure in the combustion chamber 9. The injection pressure is—depending on the selected testing conditions—between 400 and 2000 bar.

With such piezo injectors, an accurately defined fuel amount can be atomized at a certain time for a defined duration.

The injection nozzle 7 is connected to the control unit 14. The control unit 14 includes a signal generator with a downstream analogous precision current end stage in order to provide to the piezo injector a certain charge amount during the injection process.

The cylindrical combustion chamber 9 is provided with a heating chamber 8 preferably with an electric resistance heater, whereby a uniform heating of the cylinder wall can be ensured.

The electric heater is surrounded by a heat insulating structure in order to minimize the heat losses of the apparatus.

The heater of the electrically heated combustion chamber 8 is connected to an independently operating electronic temperature controller 12 which includes an electric power controller. The temperature controller 12 includes one or more temperature sensors which determine the temperature in the interior of the combustion chamber and/or in the combustion chamber wall. With this independently operating control mechanism, the air temperature in the combustion chamber interior can be adjusted to a predetermined temperature with a tolerance<1° C.

The temperature controller 12 is connected to the control unit 14 which provides the desired value and to which the actual values are transmitted.

The cylindrical pressure-resistant combustion chamber 9 has an interior volume of 500 to 1200 ml, preferably 600 to 800 ml.

As construction materials for the combustion chamber, heat- and re-carburization resistant steels are suitable which cover the full possible operating range of the test apparatus such as chamber pressures from 10 to 100 bar and air temperatures of 300 to 730° C.

The combustion chamber consists of components comprising either a combustion chamber pot with a removable circular bottom plate or a combustion chamber cylinder with removable circular top and bottom plates.

The combustion chamber interior space 10 is in communication with the ambient by way of the computer controlled exhaust valve V2. It is opened at the end of a measuring cycle in order to release the combustion gases.

Upon filling of the combustion chamber with compressed air, the pressure is controlled by an independently operating pressure controller 13, which receives the desired value from the control unit and transmits the actual value to the control unit.

Selectively a highly dynamic quartz pressure sensor 11 for sensing rapid pressure increases is mounted to the combustion chamber 10 so that it is flush with the combustion chamber wall or recessed. The pressure sensor 11 is adapted to determine the point in time of the fuel ignition and is connected to the control unit 14. The control unit 14 includes a transient recorder with a preamplifier for the conditioning of the charge signal of the quartz pressure sensor. In this connection, the measuring chain consisting of the components quartz pressure sensor—preamplifier—transient recorder are so tuned to one another that, with a digitalization of the pressure signal a time resolution of preferably better than 10 µs is obtained. The pressure sensor 11 includes a cooling sleeve through which a heat exchange liquid, preferably water, is conducted.

All the operating and measuring steps of a measuring cycle are controlled by the control unit 14 via a corresponding software program and are performed fully automatically.

The apparatus includes highly pressure-resistant connecting lines extending from the outlet of the supply pump 3 up to the inlet of the injection nozzle 7. Preferably, the connecting lines are stainless steel capillary lines as they are common in the HPLC field. As a result, the dead volume is small. All components which come into contact with the fuel, including the sample supplier 1 and the supply pump 3 may be separately temperature-controlled. In this way, the cetane number can be determined also for viscous diesel fuels such as plant oils.

The apparatus described has a number of advantageous over prior art apparatus:
  The cetane number can be determined also for relatively small samples since the apparatus has only a small dead volume,
  Because of the high injection pressures used different surface tensions of otherwise identical fuel samples have no detrimental effects.
  An automatic unsupervised testing procedure is possible.
  With the accurate control of the fuel temperature, the combustion chamber temperature and the combustion chamber pressure, the injection time and injection duration, a very good precision and repeatability can be achieved in the cetane number determination.

Typical areas of commercial applications for the apparatus according to the invention are for example:
  The continuous cetane number determination in the manufacture of refinery products.
  The cetane number determination of intermediate distillates in commercial laboratories.
  The cetane number determination of special fuels such as GTL fuels.
  The cetane number determination of mixtures of fossil diesel fuels and bio-fuels.
  The examination of the effects of fuel additives such as ignition accelerators.
  The examination in accident situations where only small fuel amounts are available.

The automatic determination of the cetane number by means of an apparatus according to the invention occurs essentially with the following method steps:

S1: Selection of a fuel sample: In the control unit 14, a listing of all the fuel samples and their storage locations in the sample provider 1 is stored. A particular sample is selected in a program-controlled manner and the suction line of the supply pump 3 is placed into communication with the storage location of the sample under the control of the control unit.

S2: Filling of the apparatus with fuel: With the high-pressure valve V1 open, the fuel pump 3 draws in the selected sample and pumps it until the line volume is flushed. Then the high pressure valve V1 is again closed. In addition, it may subsequently be necessary to flush the injection nozzle at pressures of <50 bar.

S3: Fuel pressure build up: The fuel supply pump 3 receives from the control unit 14 the desired injection pressure value which is then independently established by the fuel supply pump.

S4: Establishing a defined air pressure in the combustion chamber: The temperature controller 12 receives from the control unit 14 the desired temperature value for the combustion chamber interior 10. This value is then automatically adjusted.

S6: Determination of the ignition delay time: By checking the automatically operating control members (fuel supply pump 3, temperature controller 12 and pressure controller 13), the control unit 14 examines whether all desired values are within predetermined limits. Subsequently, the injection procedure is initiated by the control unit 14. To this end, a predefined current signal is supplied to the injection nozzle 7, which is in the form of a piezo injector, in such a way that the injection duration and the valve lift of the injection nozzle obtain predetermined values.

The begin of the fuel injection (time value) is recorded by the control unit. At the same time, the control unit 14 records the time-dependent pressure in the combustion chamber interior as sensed by the pressure sensor 11. The time difference between injection begin and the begin of the pressure increase is used as the ignition delay for the calculation of the cetane number.

S7: Discharge of the exhaust gas: The control unit 14 interrupts the gas supply to the combustion chamber interior 10 by way of the pressure controller 13 and opens the exhaust gas valve V2.

The steps S3 to S7 are repeated at least once. From the individual results, an average cetane number of the fuel sample is then calculated. Subsequently, the procedure described is required beginning with the selection of a new fuel sample.

The method steps described are sequentially executed. Some of the method steps such as the steps S3, S4 and S5 may also be concurrently executed.

What is claimed is:

1. An apparatus for determining the cetane number of a fuel, comprising: a constant-volume combustion chamber (9), a fuel injection nozzle (7) in the form of a temperature controlled injector mounted onto the combustion chamber for injecting fuel into the combustion chamber (9), means (11) for filling the combustion chamber (9) with compressed air, means (8) for heating the combustion chamber (9) and means (11, 14) for recording the pressure generated in the combustion chamber (9) during ignition and combustion of fuel injected into the combustion chamber (9), an automatic sample supplier (1) for storing and supplying fuel samples whose cetane numbers are to be determined, and a high pressure pump (3) for pressurizing a selected fuel sample and supplying it to a high pressure fuel storage (5) which is connected to the fuel injection nozzle (7) for injection of the high pressure fuel into the combustion chamber (9) via the fuel injection nozzle (7).

2. An apparatus according to claim 1, wherein the automatic sample supplier (1) includes a plurality of selectively accessible sample containers (1').

3. An apparatus according to claim 1, wherein the injection nozzle (7) is surrounded by a cooling sleeve (6) through which a temperature-controlled liquid is conducted for maintaining the injection nozzle (7) at a predetermined temperature.

4. An apparatus according to claim 3, wherein the cooling sleeve (6) is self-supporting and removably disposed around the combustion chamber (9).

5. An apparatus according to claim 1, wherein the high pressure pump (3) is a piston compression pump with integrated pressure control.

6. An apparatus according to claim 1, wherein the fuel injection pressure at which the sample fuel is injected into the combustion chamber (9) is between 400 and 2000 bar.

7. An apparatus according to claim 6, wherein the fuel injection pressure is 800 to 2000 bar.

8. An apparatus according to claim 1, wherein the combustion chamber (9) is provided with a sleeve uniformly extending around the combustion chamber (9) and including an electric resistance heater (8) and a temperature controller (12).

9. An apparatus according to claim 1, including a control unit (14) for controlling operation of the various components of the apparatus.

10. An apparatus according to claim 9, wherein the combustion chamber (9) is provided with a quartz pressure sensor (11) in communication with the control unit (14) for recording the pressure in the combustion chamber (9).

11. A method for determining the cetane number of a fuel in an apparatus for determining the cetane number of a fuel, comprising: a constant-volume combustion chamber (9), a fuel injection nozzle (7) in the form of a temperature controlled injector mounted onto the combustion chamber for injecting fuel into the combustion chamber (9), means (11) for filling the combustion chamber (9) with compressed air, means (8) for heating the combustion chamber (9) and means (11, 14) for recording the pressure generated in the combustion chamber (9) during ignition and combustion of fuel injected into the combustion chamber (9), an automatic sample supplier (1) for storing and supplying fuel samples whose cetane numbers are to be determined, and a high pressure pump (3) for pressurizing a selected fuel sample and supplying it to a high pressure fuel storage (5) which is connected to the fuel injection nozzle (7) for injection of the high pressure fuel into the combustion chamber (9) via the fuel injection nozzle (7), said method comprising the steps of:

a) selecting a fuel sample of the fuel sample supplier (1),
   b) pumping the fuel of the fuel sample to the storage device (6) while increasing the pressure of the fuel pumped to a desired fuel injection pressure,
   c) providing in the combustion chamber a charge of compressor air of a predetermined pressure and a predetermined combustion chamber temperature,
   d) initiating the injection of fuel into the combustion chamber (9) while sensing the pressure in the combustion chamber and recording it,
   e) determining the cetane number of the combusted fuel from the pressure recorded over time, and
   f) releasing the gas from the combustion chamber.

12. A method according to claim 11, wherein the steps b to f are repeated several times and the cetane number of the fuel sample is determined from a combination of the several measurements.

* * * * *